(12) United States Patent
Rounds et al.

(10) Patent No.: US 9,541,491 B2
(45) Date of Patent: Jan. 10, 2017

(54) TEST METHODS AND DEVICE FOR MEASURING TRANSIENT RESISTANCE TO MOVEMENT

(71) Applicants: Phillip Nelson Rounds, Flemington, NJ (US); Rhyta Sabina Rounds, Flemington, NJ (US)

(72) Inventors: Phillip Nelson Rounds, Flemington, NJ (US); Rhyta Sabina Rounds, Flemington, NJ (US)

( * ) Notice: Subject to any disclaimer, the term of this patent is extended or adjusted under 35 U.S.C. 154(b) by 261 days.

(21) Appl. No.: 13/865,196

(22) Filed: Apr. 18, 2013

(65) Prior Publication Data

US 2014/0311210 A1    Oct. 23, 2014

(51) Int. Cl.
*G01N 19/02* (2006.01)

(52) U.S. Cl.
CPC ..................... *G01N 19/02* (2013.01)

(58) Field of Classification Search
CPC ..................................................... G01N 19/02
See application file for complete search history.

(56) References Cited

U.S. PATENT DOCUMENTS

| 4,133,200 | A | * | 1/1979 | Cray | G01N 33/30 |
| | | | | | 73/10 |
| 5,115,664 | A | * | 5/1992 | Hegde | G01N 19/02 |
| | | | | | 360/137 |
| 5,132,906 | A | | 7/1992 | Sol et al. | |
| 5,679,883 | A | * | 10/1997 | Wedeven | G01N 3/56 |
| | | | | | 73/10 |
| 6,015,192 | A | | 1/2000 | Fukumura | |
| 6,094,967 | A | * | 8/2000 | Cavdar | G01N 19/02 |
| | | | | | 73/9 |
| 6,105,415 | A | | 8/2000 | Kenney | |
| 6,119,505 | A | | 9/2000 | Sullivan et al. | |
| 6,349,587 | B1 | * | 2/2002 | Mani | G01N 19/02 |
| | | | | | 73/9 |
| 6,857,306 | B2 | | 2/2005 | Domeier | |
| 7,013,713 | B2 | | 3/2006 | Webster et al. | |

(Continued)

FOREIGN PATENT DOCUMENTS

GB    2404032    1/2005

OTHER PUBLICATIONS

Müller, Markus T., et al. "Lubrication properties of a brushlike copolymer as a function of the amount of solvent absorbed within the brush."Macromolecules 38.13 (2005): 5706-5713.*

(Continued)

*Primary Examiner* — Robert Huber
*Assistant Examiner* — Herbert K Roberts

(57) ABSTRACT

A device for transient measurement of motion resistance between test substance and one or two test surfaces, comprising a tension/compression force transducer, a speed and/or torque controlled motor with position encoder, rails for mounting a movable sled, method for applying a normal force on the test specimen and computerized data acquisition. The tension/compression force transducer is capable of measuring the transient resistance to motion of the sample mounted to the movable sled in either horizontal direction or in reversible motion oscillatory pull/pull direction at variable frequency and amplitude. The force transducer is capable of precise measurement of the full motion record of the test material from the initiation of motion to the steady state movement.

18 Claims, 14 Drawing Sheets

(56) References Cited

U.S. PATENT DOCUMENTS

| | | |
|---|---|---|
| 8,151,625 B2 | 4/2012 | Ebrecht |
| 8,342,032 B2 | 1/2013 | Debon et al. |
| 8,371,182 B1 | 2/2013 | Israelachvili |
| 2007/0288186 A1* | 12/2007 | Datta ............ G01N 19/02 73/9 |
| 2009/0198159 A1* | 8/2009 | Linzell ............ A61H 7/003 601/138 |

OTHER PUBLICATIONS

John A. Nairn and Tong-Be Jiang, Measurement of the Friction and Lubricity Properties of Contact Lenses, Proceedings of Antec 95, May 7-11, 1995, Boston, MA.

Stephen Michielsen, Device for Measuring Sliding Friction on Highloft Nonwovens, Journal of Engineered Fibers and Fabrics, vol. 1, Issue 1 (2006).

J. Ghorieshi, A. Sharma, F. Lopresti, M. Ghorieshi, Temperature Measurement at the Polymer-Metal Contact: A Tribometer Design, Proceedings of the ASEE New England Section 2006 Annual Conference.

K. J. Hughes, V. F. Lvovich, J. Woo, B. Moran, A. Suares, M.Hang, T. Truong, Novel methods for emollient characterization, Cosmetics and Toiletries Manufacture Worldwide, Mar. 27, 2006.

A.C. Rennie, P.L. Dickrell and W.G.Sawyer. Friction coefficient of sofft contact lenses: measurements and modeling. Tribology Letters, vol. 18, No. 4, Apr. 2005.

Angle, J. Coefficient of Friction of Eye Drop Solution. Nanovea. 2010.

ASTM D1894. Standard Test Method ror Static and Kinetic Coefficients of Friction of Plastic Film and Sheeting. ASTM West Conshohocken, PA.

ASTM F609. Standard Test Method for Using a Horizontal Pull Slipmeter (HPS). ASTM, West Conshohocken, PA.

PCS Instruments. HFRR High FRequency Reciprocating Rig. Brochure.

Redfern, M.S., Marcotte, A., Chaffin, D.B. A Dynamic Coefficient of Friction Measurement Device for Shoe/Sloor Interface Testing. Journal of Safety Research. vol. 21, pp. 61-65, 1990. National Safety Council and Pergamon Press.

Roba, M., Duncan, E.G., Hill G.A. Friction Measurements on Contact Lenses in Their Operating Environment. Tribology Letters (2011) 44387-397.

\* cited by examiner

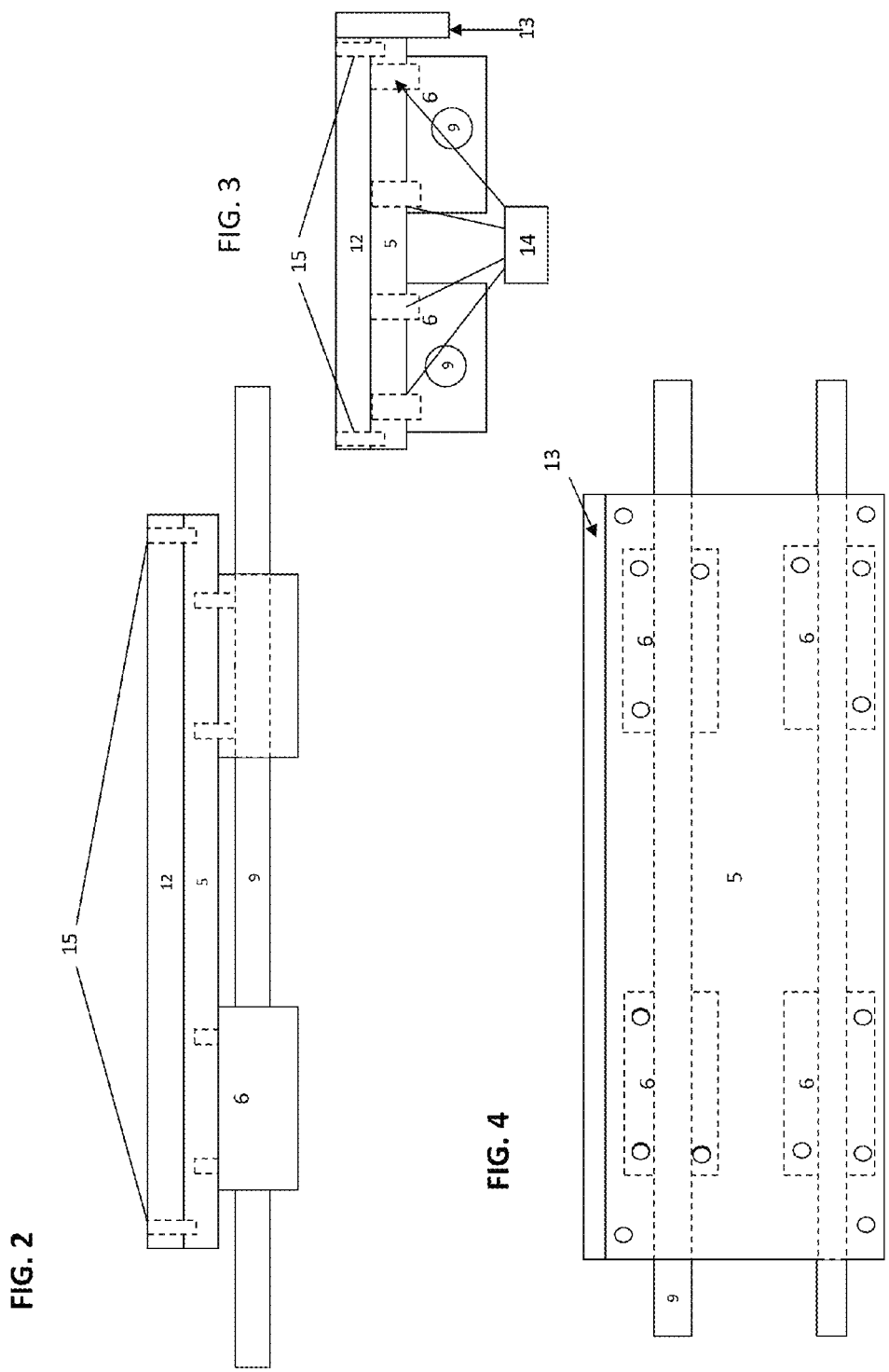

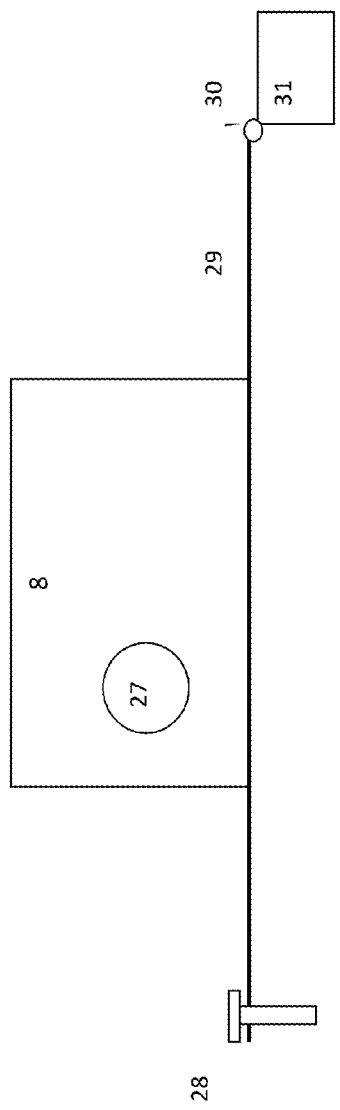
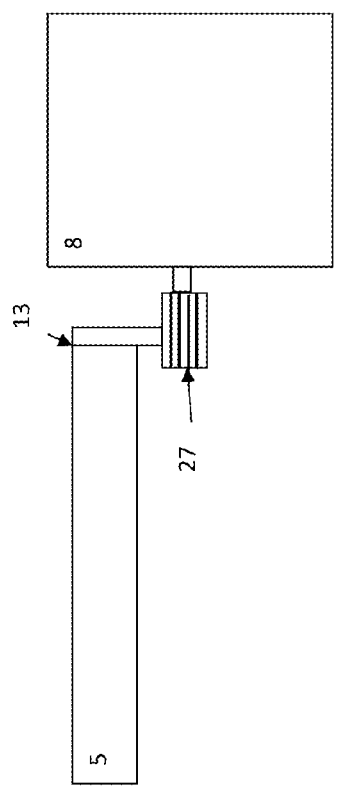

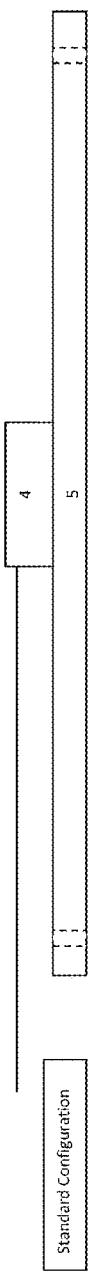
FIG. 7 Standard Configuration
FIG. 8 Rigid substrate
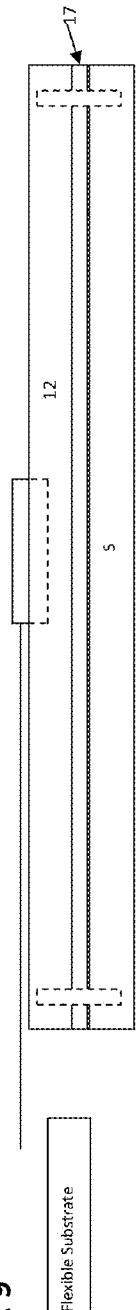
FIG. 9 Flexible Substrate
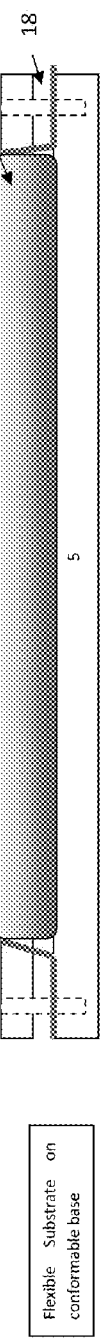
FIG. 10 Flexible Substrate on conformable base
FIG. 11 Flexible Substrate on rigid or conformable base, reservoir for surfeit of lubricant

TEST METHODS AND DEVICE FOR MEASURING TRANSIENT RESISTANCE TO MOVEMENT

CROSS-REFERENCE TO RELATED APPLICATIONS

Provisional Application No. 61/625,906, filed on Apr. 18, 2012.

STATEMENT REGARDING FEDERALLY

Not applicable

REFERENCE TO A COMPACT DISK

Not applicable

TECHNICAL FIELD

This invention relates to the transient measurement of fluid and soft solid attributes such as spreadability, ease of application, adsorption, lubricity and coefficient of friction dynamically. Unlike conventional lubricity and coefficient of friction measurements and devices, this invention follows the change in transient motion resistance throughout the intended use of the test substance. An important improvement of this device is the ability to follow transient motion resistance of compliant substrates and/or changes in test substances when tested in an open or closed environment. A further improvement in the device is its versatility in being able to operate under various test conditions such as constant velocity, constant force, or progressive increase in force using test substrates that are rigid, flexible, or conformable.

BACKGROUND OF THE INVENTION

Known methods of measuring coefficient of friction consist of force transducers or gauges and linear or rotational motors for dragging test materials and/or tools across test substrates. Examples include tire friction on road services, as disclosed in U.S. Pat. Nos. 5,132,906 and 6,015,192 tire and road surface friction applications. Additional inventions include devices for testing lubricity of fluids in drilling muds for oil wells as in U.S. Pat. No. 6,105,415 and fuels, as in GB2404032A, and U.S. Pat. No. 7,013,713. Many of these methods and devices are tribology science instruments related to wear on impinging surfaces. Further, the Horizontal Slip Meter is a typical device as detailed in ASTM F609 for the friction measurement of foot wear, for example, on dry walkway surfaces and the High Frequency Reciprocating Rig is a friction and wear instrument typically used for fuels and lubricants. ASTM D1894 describes static and kinetic coefficient measurements for plastic film and sheeting.

Various tribology test methods teach the use of single or multiple balls, pin on disc, ball on disc, plate on disc for estimates of friction on wet or dry surfaces with or without surface modifications. A four-ball wear and friction test apparatus is taught in U.S. Pat. No. 6,857,306. Regardless of the test configuration and test geometry, the primary objective is not one that focuses on the total motion of the test material. Typical data results show Force vs Speed or Stribeck curves of coefficient of friction. Data output appears to be based on steady state equilibrium measurements or the assumption of steady state. Friction factors as a function of speed using a ball on triple pad device is disclosed in U.S. Pat. No. 8,342,032.

In many mechanical and biological applications, the full motion of the test system is relevant and steady state is never fully achieved. For systems that include compliant, deformable surfaces, the full motion is frequently critical in understanding the benefit of lubricants, surface treatments, polishes, etc. This includes not only the static and dynamic friction coefficients, but the deformation of the soft substrates before bulk motion is observed. Examples of this include the application of a topical to a body surface. This can be lip treatment/colorant, a lotion or cream or gel to a body surface, a lubricant for medical examinations, rash treatments, optical treatments, etc. The initial resistance to motion of the physiological surface is critical to the application of the product as this can cause discomfort or damage to the skin surface. Further examples include the shear resistance of adhesives to shearing motion. Ultimate failure of this surface can be complex, dependent on the strength of the substrate/adhesive bond, the thickness of the adhesive layer and its stiffness, humidity, temperature, etc. An entire measurement profile from the application of a normal and horizontal force, its creep, yield and dislocation falls outside the scope of most coefficient of friction, lubricity, or tribology instruments. Another example is related to the motion of the eye in the absence and presence of lubricants and other medicaments or in the presence of corrective contact lenses. Nairn and Jiang in "Measurement of the Friction and Lubricity Properties of Contact Lenses" present results in terms of Stribeck curves of the coefficient of friction as a function of Sommerfeld Number and show both normal and frictional force curves as a function of time. The data shows that the emphasis is not on the repetitive onset of blinking eye movement nor on the transient nature of the motion. Friction Abrasion Analyzer Triboster (TS-501) by Kyowa Interface Science Co manufactures a friction device that operates in the horizontal plane in a linear or reciprocating manner. Abrasion data output is friction coefficient as a function of cycles employing flat, point, facet, line contact parts. Data output is in terms of coefficient of friction as a function of cycles. U.S. Pat. No. 8,342,032 teaches a Tribology Device for Assessing Mouthfeel Attributes of Foods. This ball-on-three-plates rotational tribology device uses a thermoplastic polymer as an integral part and measures friction factors as a function of sliding speed.

Regardless of the nature of the testing materials or test substrates, the lubricity metrics and tribology have been focused on coefficient of friction measurements and not the total deformation/resistance curves. In fact, compliance of the substrates is often experimentally minimized, as cited by Michielsen in working with fabric matting and foams. The coefficient of friction is recited as data output from the device. Further, coefficient of friction of soft contact lenses is measured by Rennie et al. This comprehensive study provides coefficient of friction measurements as a function of numerous variables without reference to the time record of the force measurements. The lack of robust data acquisition appears to be the principle deficiency of current methodologies and devices. Lubricity, as a measure of skin feel, was measured as a coefficient of friction between two surfaces with a reciprocating teflon blade by Hughes, Lvovich, Woo, Moran, Suares, and Truong. The change in coefficient of friction during spreading with absorption of the emollient and evaporation is not measured. The Nanovea Tribometer using alumina ball and glass slides, measures coefficient of solutions and provides time based force results, using a flat or sphere shaped indenter and rotational disk. Wear coefficients are calculated with varying time, contact pressure, velocity, and other variables.

BRIEF SUMMARY OF THE INVENTION

One embodiment of the invention is a device for measuring the resistance to motion between one or two test surfaces and a test material. This device comprises a frame, a tension/compression force transducer, and torque controlled motor with encoder, a test sled, guide rails for test sled, mounting brackets for removable test substrates. More importantly, the force needed to produce motion in any of the contact surfaces, solid or liquid, can be determined. Data output from device is the full time registry of force as a function of time or position as a function of force and/or time.

The invention is a device intended to experimentally simulate the physics of motion resistance involving fluids and or soft solids with rigid and/or deformable substrates. The objective of this device is a laboratory metric for use in pharmaceuticals and OTC product development in female health, eye care, oral care, skin care and other applications. The ability to focus on the transient flow behavior is likely to show merit in the assessment of mouthfeel and similar sensory attributes and the act of swallowing when drinking, for example, is a rapid transient flow. In oral care, specific applications may be dental impression materials or adhesives. Another embodiment of the invention is to measure dislodge forces between one or two mating surfaces.

BRIEF DESCRIPTION OF THE SEVERAL VIEWS OF THE DRAWINGS

FIG. 2 Front view of the transport plate assembly.

FIG. 3 Side view of the transport plate assembly.

FIG. 4 Top view of the transport plate assembly.

FIG. 5 Front view of the motor assembly.

FIG. 6 Side view of the motor assembly attached to the transport plate.

FIG. 7 Side View mounting configuration for rigid test substrates in an embodiment of the invention.

FIG. 8 Alternative side view mounting configuration for rigid test substrates in an embodiment of the invention.

FIG. 9 Side view mounting configuration for flexible and/or deformable test substrates in an embodiment of the invention.

FIG. 10 Side view mounting configuration for flexible, conformable and deformable test substrates in an embodiment of the invention.

FIG. 11 Side view mounting configuration for flexible, conformable and deformable test substrates in a surfeit of fluid in an embodiment of the invention.

DETAILED DESCRIPTION OF THE INVENTION

This invention relates to a multifunctional apparatus for measurement of slip, drag, flow resistance or coefficient of fraction or lubricity between one or two rigid test surfaces, or flexible test surfaces or one rigid and one flexible/conformable surface or combination thereof either in the dry state or in the presence of a fluid layer or pool in the x-y horizontal plane. Since there is some confusion regarding terms such as lubricity, the general object of this invention is a device for the measurement of motion resistance between two rigid, flexible, conformable and/or deformable contact surfaces in the horizontal plane with the ability to compare dry vs motion in the presence of a fluid or surface modification. High and low energy test surfaces are incorporated in the design of the device to simulate resistance to motion of natural, biological, mechanical or physiological members or components thereof. Laminated conformable and deformable test surfaces that are hydrophobic or hydrophilic are included to simulate and predict ease of application of medicaments, lotions, creams and oils to skin surfaces, in one embodiment, or ocular surfaces, in another embodiment. Test surfaces of the device can be of low costs and disposable or custom fabricated as dictated by the objective of the measurement.

Figure 1:
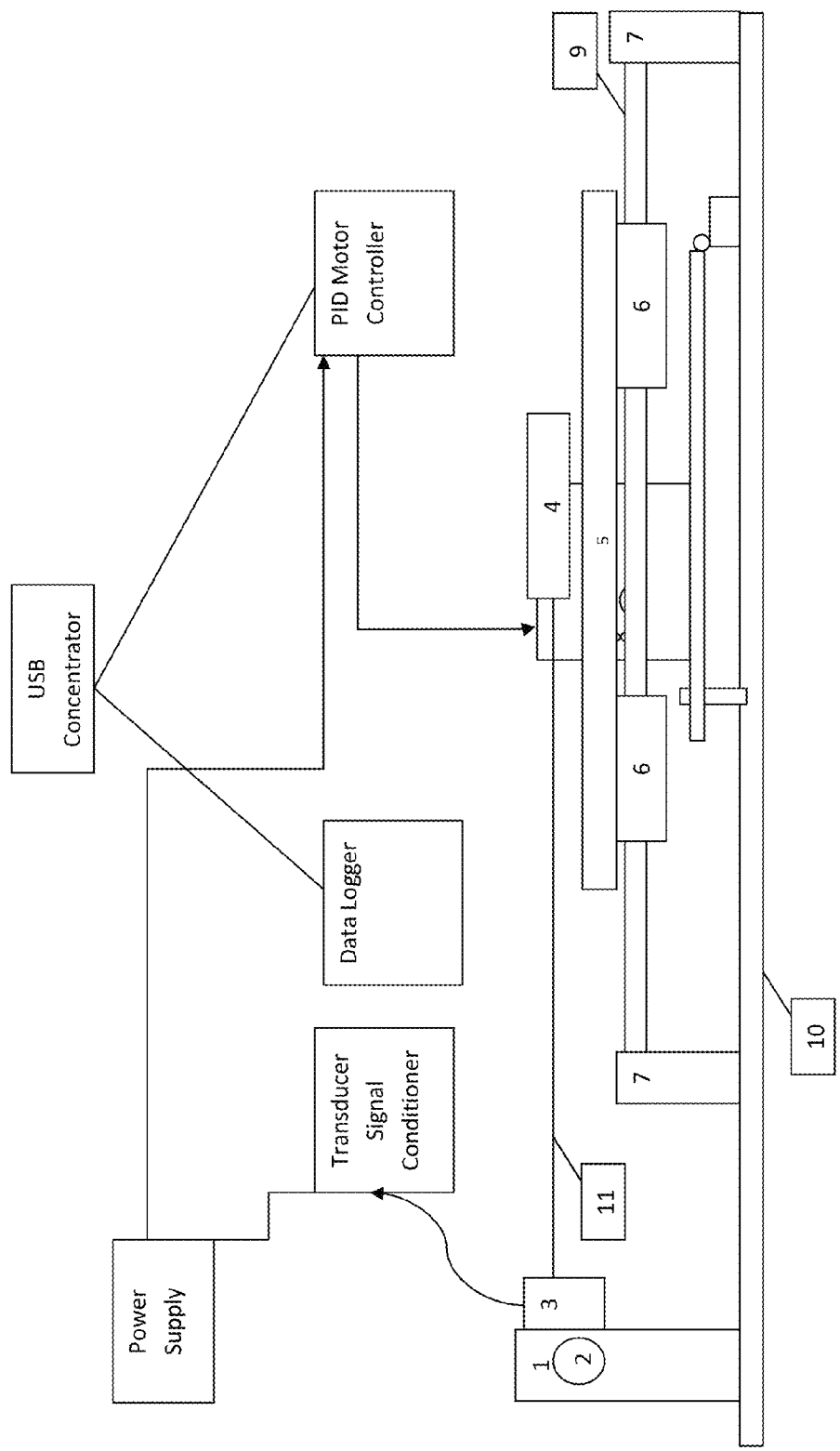
FIG. 1 Side view of the apparatus in accordance with an embodiment of the invention.

The device consists of components identified in FIG. 1. Resistance to motion between one movable test surface or transport plate assembly (5) and one stationary test surface or sensor plate (4) is measured using a sensor (3), as a tension/compression force transducer (3). The transducer (3) is rigidly connected to the sensor plate (4). The transducer is rigidly mounted to a z-axis mount (1), raised and lowered by the vertical control knob (2). The z-axis mount (1) is attached to the base plate (10) of the entire apparatus. The transport plate assembly (5) is mounted on high-precision linear motion bearings (6), in turn mounted on polished linear rods (9), which in-turn are held in place by pillow blocks (7) mounted on the base plate (10). Both the assembly (5) and the sensor plate (4) contain levels to maintain parallelism. Provisions are provided for adding normal force to the sensory plate (4). Motion or force is controlled with a motor assembly (8) which can provide optionally a constant velocity motion, an accelerated motion, or a large or small oscillatory motion along the guide mount rails (9) and the precision linear motion bearings (6) of the device. Motion can be controlled by torque or speed. The PID motor controller slows for precise motor and motion control along the horizontal plane, either speed or torque controlled. The sensor is equipped with a mounting block with height adjustable stage (1,2). Motion, especially at the start and stop of motion, is accurately controlled to investigate the slip and/or stick phenomena and the transition from static to dynamic friction. The device allows for tests to be programmed with multiple motion sequences in steady velocity motion, with accelerated and decelerated movement, and pauses or motion delays, for example. An important design element of this device is the ability to control the travel, the length of delays, and the resumption of movement. Movement can also be reversed with large and small amplitude oscillations. In a preferred embodiment, total motion travel can also be independently controlled or limited by motor torque/force in horizontal motion.

Figure 13:
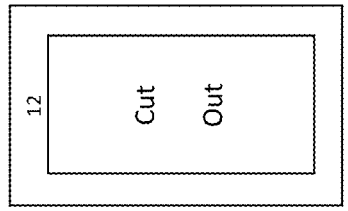
FIG. 13 Top view alternative sample retainer for mounting to the transport plate assembly in an embodiment of the invention.
Figure 12:
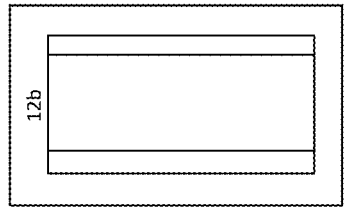
FIG. 12 Top view of retainer for mounting to the transport plate assembly in an embodiment of the invention.
Figure 14:
FIG. 14 Side view standard configuration of a rigid sensor plate in an embodiment of the invention.
Figure 15:
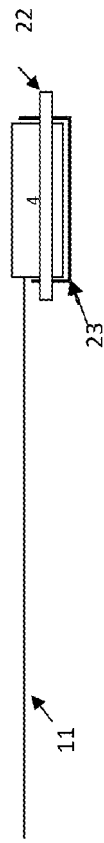
FIG. 15 Side view configuration of a rigid sensor plate with a flexible testing substrate attachment using a retaining ring one embodiment of the invention.
Figure 16:
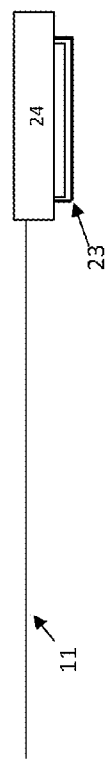
FIG. 16 Side view mounting configuration of a rigid sensor plate with a flexible testing substrate attachment using a concentric annular ring in an embodiment of the invention.
Figure 17:
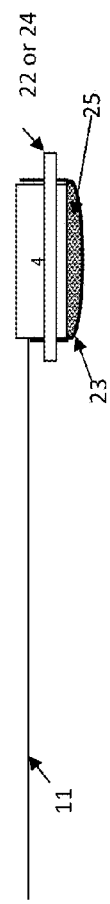
FIG. 17 Side view mounting configuration of a rigid sensor plate with a deformable, conformable laminated testing substrate attachment using a retaining ring or concentric annular ring in an embodiment of the invention.
Figure 18:
FIG. 18 Side view mounting configuration of a rigid sensor plate to which a test substrate has been attached in an embodiment to the invention.

The transport plate assembly (5) and the sensor plate (4) in FIG. 1 are design to easily mount a wide range of test surfaces. The transport plate assembly is shown in detail in FIGS. 2, 3 and 4 from top and side views. This assembly can hold a wide range of materials including rigid metals, rigid plastics, glasses, ceramics, polymer films, and foams. FIG. 2 and FIG. 3 show the transport sled with the optional Sample Holder (12) in place, attached to the transport sleds with finger screws (15). FIG. 3 and FIG. 4 also show the drive rack (13) which connects to the motor assembly, itself shown in FIG. 5 and FIG. 6. The motor assembly (8) is mounted on a plate (29). The plate (29) is affixed to the base plate (10) not shown, by a hinge (30) connected to a block (31) which is attached to the base plate. At the other end of the motor plate (29) are two spring-loaded bolts providing for height adjustment of the motor assembly (8) relative to the base plate. FIG. 6 shows the motor drive assembly and the connection to the transport plate (5) via drive rack (13) and the pinion gear (27) mounted to the motor assembly (8). Examples are provided in FIG. 7 through FIG. 11 for the mounting of various test substrates, rigid, flexible, conformable and/or deformable, using a form insert, in one example. FIG. 7 depicts mounting a test substrate (16) to the transport plate (5) using screw holes in the transport plate. FIG. 8 depicts using the device without any modifications to the test surfaces. Mounting hardware for conformable substrates with and without a reservoir for liquid addition is provided in FIG. 9 to FIG. 11. FIG. 9 depicts a flexible substrate (17) mounted on the transport plate (5), held in place by an optional mounting plate (12,12b). FIG. 10 depicts a flexible substrate (19) mounted on a deformable or conformable under-body (18), held in place by the optional mounting plate (12). FIG. 11 depicts a flexible substrate (21) affixed to the optional mounting plate 12b (20) providing for testing within a reservoir of fluid. Examples are provided in FIG. 12 and FIG. 13 of upper mounting plates. FIG. 12 depicts an example of an upper mounting plate to hold a sample submerged in a fluid. FIG. 13 depicts an upper mounting plate to hold a flexible test material. FIG. 14 to FIG. 18 shows comparable mounting arrangements for the mating sensor plate (4) for various test substrates, either rigid, flexible, conformable and/or deformable, using a foam insert, in one example. Transport assembly and sensor plate are sized to the specifics of the testing needs and transducer sensitivity. FIG. 14 presents the basic configuration, the upper plate (4) and the attaching rod (11) connecting it to the force transducer. FIG. 15 presents on method of attaching an optional test surface (23) to the upper plate (4) via spring clips (22). FIG. 16 present an alternative method for attaching an optional test surface (23) to the upper plate (4) via an annular ring (24).

In biological, cosmetic and personal care applications, the device can be used to measure the resistance to application of a lotion, cream to a simulated or actual skin surface. The laminated test substrates with flexible, conformable, and deformable components are intended to simulate, for example, the effect of topical, gynecological or oral treatments on body parts, for example, in one embodiments, such as the face, the legs, the arms, the hands, the mouth, etc. Porous substrates can also be used to measure speed of absorption of said application to the simulated or actual skin surface to determine the effect on motion resistance. In another embodiment of the invention, the removal of said lotions and creams can also be tested for resistance to motion during removal in the presence of water or other solvents. Washout of ocular lubricants can also be measured using the device in manner using appropriate aqueous media.

Figure 19:
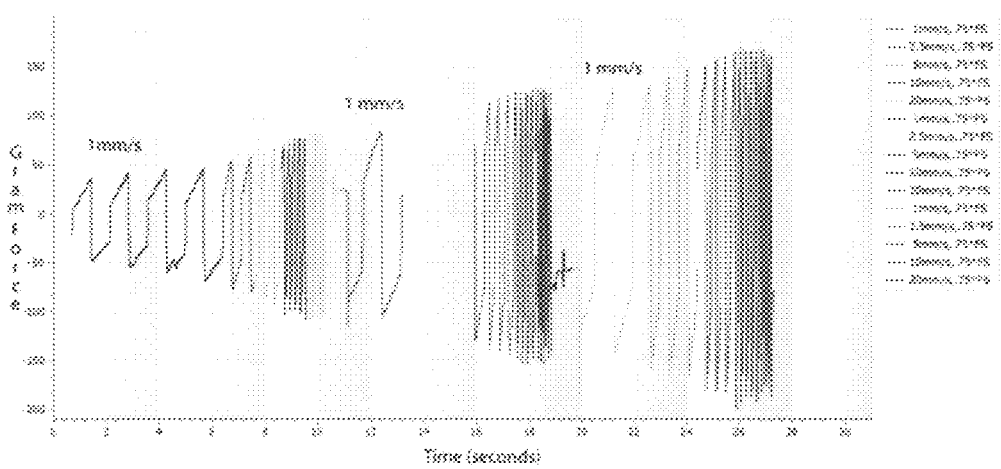
FIG. 19 Example graph of force as a function of time curve showing cycles at different normal forces.

FIG. 19 show the complete force-time data for an experimental measurement in push-pull cycles using a commercial skin lubricant with a vinyl test substrate over foam. Cycle frequency is controlled by sled speed in this example. The data is provided in terms of translational force at each normal force and speed. FIG. 19 shows the force as a function of time throughout the entire movement sequence at three normal forces for each cycle. Test substrate speed is progressively increased from 1.0, 2.5, 5, 10 and 20 mm/s with three applied normal forces. The importance of this test method is clearly seen in the lack of a steady state force which makes the calculation of a coefficient of friction imprecise and questionable. We are showing a steady increase in transmitted force through the entire movement of the test fluid between the substrates.

Eye lubrications and medicaments have been one of the driving forces for the development of the device of this invention due to the experimental difficulties in making these measurements. Three commercial lubricants were purchased and tested, with results provided in FIG. 20 and FIG. 25. These figures are included to provide examples of the manner in which the present invention extends beyond prior art in measuring the lubricity of such fluids.

All three products were tested identically, with three drops placed between the two plates, at room temperature, 23° C. Both test surfaces were cast acrylic with the top static surface 42 mm in diameter. Sled travel was +/−20 mm with travel speed of 10 mm/s, test duration of 200 cycles with 100 grams normal force.

Figure 20:
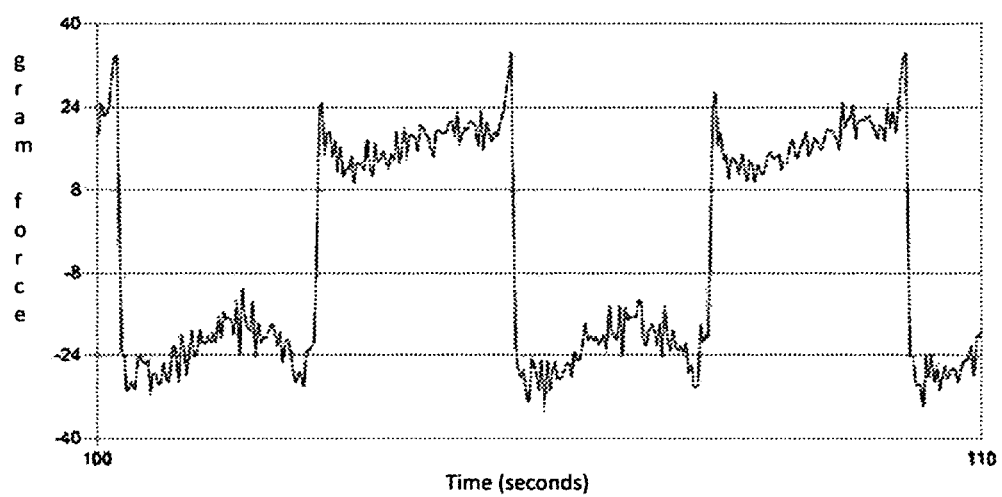
FIG. 20: Example graph of force as a function of time curve showing individual cycle trace with Eye Drop Product A as lubricant.
Figure 21:
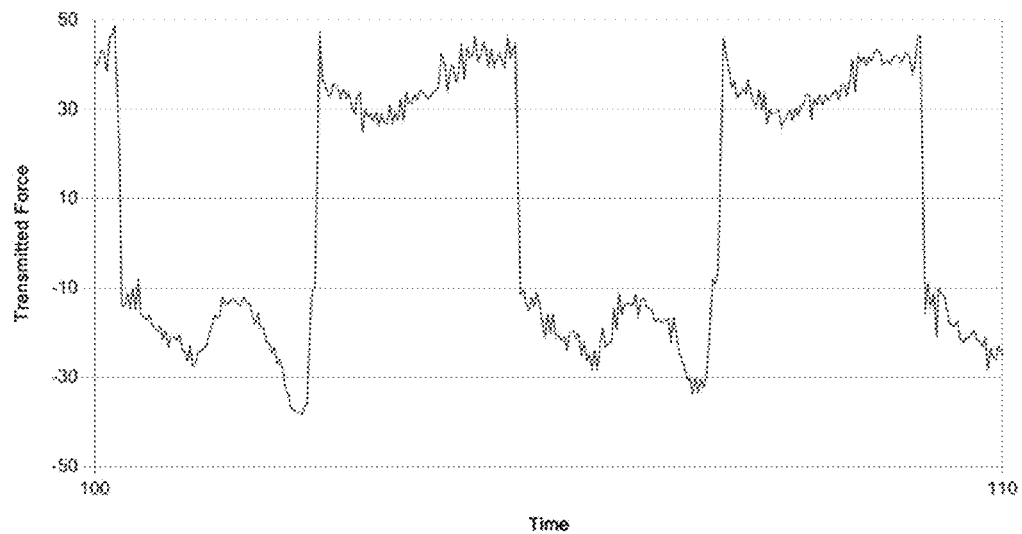
FIG. 21: Example graph of force as a function of time curve showing individual cycle trace with Eye Drop Product B as lubricant
Figure 22:
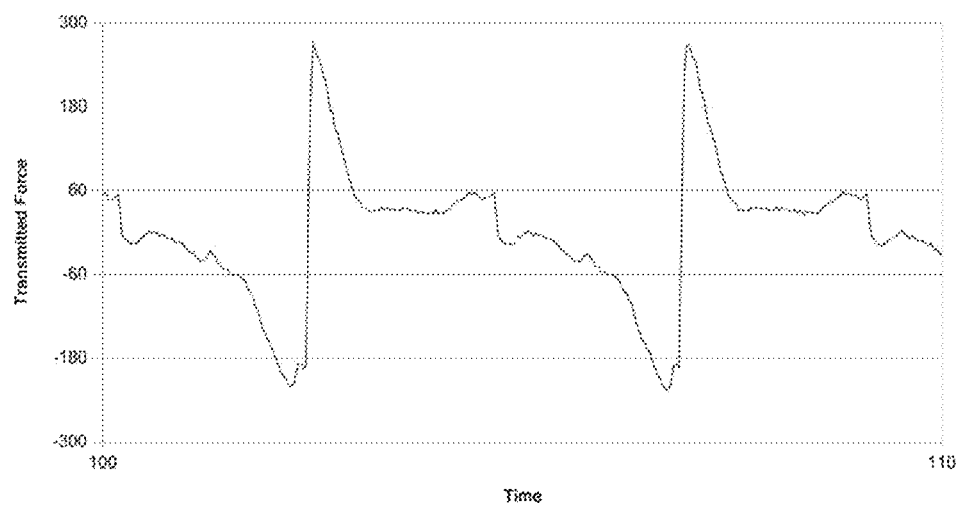
FIG. 22: Example graph of force as a function of time curve showing individual cycle trace with Eye Drop Product C as lubricant, identifying a highly structured product.

FIG. 20-FIG. 22 depict force as a function of time for the three products, Product A, Product B and Product C, respectively, for a period of two cycles, permitting direct comparison of the properties of each eye additive. In FIG. 20 Product A shows relatively uniform translational force throughout the cycle with some edge effects. The relative symmetry of the upper and lower half cycles is indicative that the product distributes or spreads and wets the acrylic surfaces well. The translational force is nearly equal between the upper and lower halves of any one cycle, confirming the uniformity of distribution, as in spreading and wetting, of the fluid as the test process itself distributes the three drops along the lower plate due to its motion. The peaks at (both) edges of the upper half cycle are indicative of slip-stick as the motion slows and reverses direction. In this test, as one embodiment of the invention, the travel of the speed is horizontal in one direction, stops, and reverses direction, for one complete cycle in the push/pull test.

FIG. 21 presents a second commercial product, Product B, showing different behavior, less uniform within one complete cycle, the result of non-uniform spreading, in this case an undesirable attribute of the product. This is shown by the lack of symmetry between the upper and lower halves of a cycle, and the different translational forces in each half of the cycle.

FIG. 22 for a third commercial product, Product C, presents a completely different curve, one with extraordinarily high and broad edge effects shown by the peaks at each end of the curve. This is a fluid with high extensional viscosity, pulling away from the edges results in a force almost three times the applied normal force. This product has been cited to cause some difficulties in consumer use causing excessive adhesion to substrates especially when contact lenses are in use.

Figure 23:
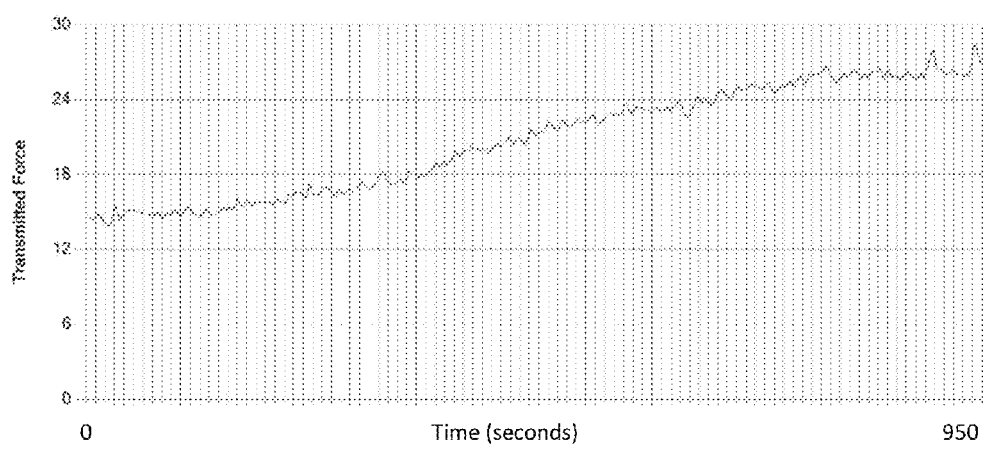
FIG. 23: Example graph of force as a function of time curve for Eye Drop Product A spanning 15 minutes showing an 80% reduction of lubricity over time.
Figure 24:
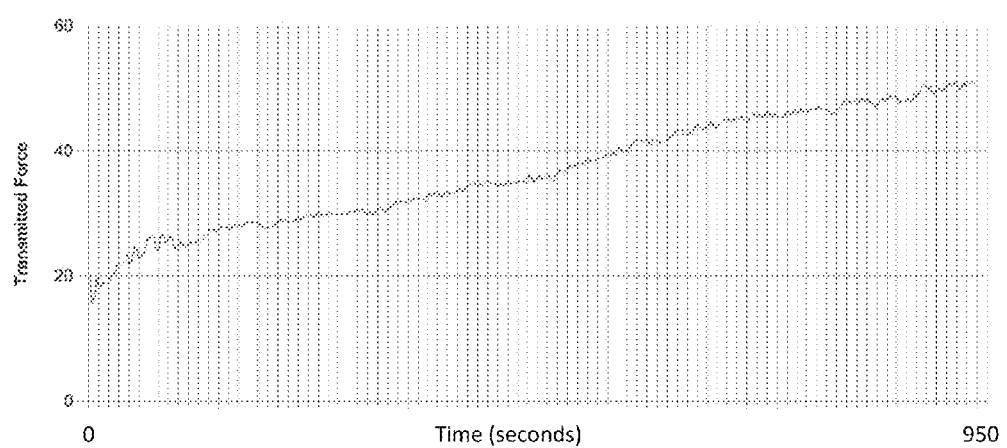
FIG. 24: Example graph of force as a function of time curve for Eye Drop Product B spanning 15 minutes showing a 150% reduction of lubricity over time.
Figure 25:
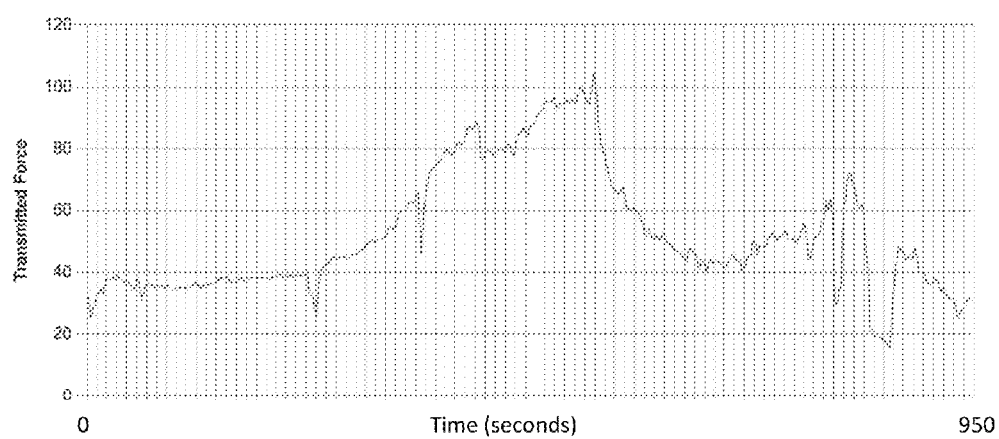
FIG. 25: Example graph of force as a function of time curve for Eye drop Product C spanning 15 minutes showing an elimination of lubricity to becoming an adhesive over time, with subsequent product failure.

FIG. 23 to FIG. 25 present the same products, Products A, B and C measured over the full fifteen minute time frame, permitting evaluation of the lubricity of these materials as their composition changes due to evaporation or other factors, and dispersion of the fluid away from the upper plate, FIG. 23 shows that Product A has a coefficient of friction (CoF) between 0.13 and 0.14 for the initial few seconds, growing to approximately 26, a decrease in lubricity of 50%, by the end of 15 minutes. FIG. 24 shows a similar, but more extreme, trend for Product B, starting with a coefficient of friction of 0.20 in the initial few seconds to over 0.5 by 15 minutes, a reduction in lubricity of over 70%. FIG. 25 representing the same test for Product C shows a drastically different curve, documenting that within 10 minutes the product actually becomes an adhesive (CoF>1), at which point the product structure fails, falls to 0.4, from which begins to climb once again, then behave erratically and totally fail.

Figure 26:
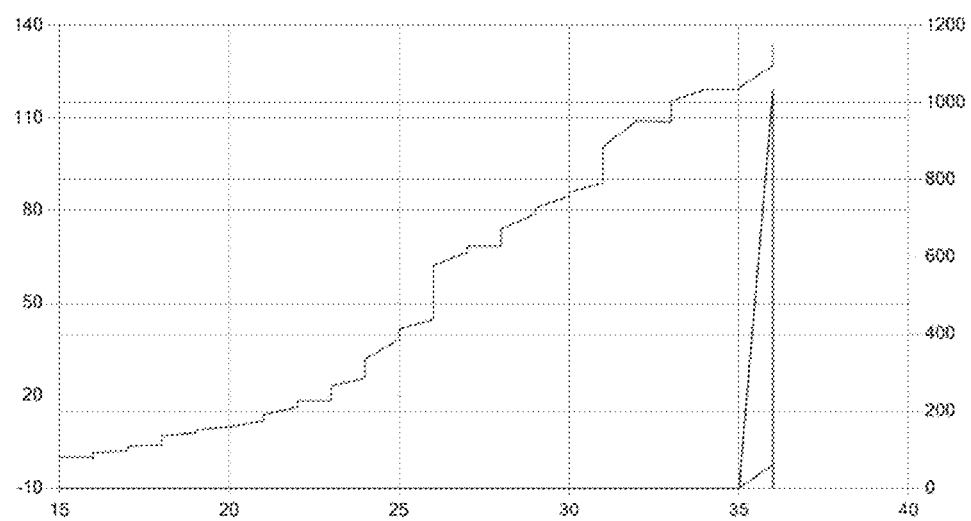
FIG. 26: Example of Static Drag Test with denture adhesive.

An additional embodiment of the invention allows for a Static Drag Test in which a substance as a liquid, soft solid or adhesive is placed between two substrates and the force to dislodge or move either of the substrates is measured. This is achieved by progressively increasing the torque of the motor engaging the sled, thereby applying a shear stress to the test object comprised of test substance and substrates. In the example embodiment, one test surface is a textured acrylic and one is a smooth acrylic surface with 100 gram normal force. Representative results are provided in FIG. 26. In this test, the lower plate, or the sled, is initially induced to move at a very low torque setting. The torque is progressively increased and the resultant translational force on the upper sensor plate is recorded. The test is considered completed when free motion of the lower plate is achieved, as measured by the average speed of the sled over a one second time period. FIG. 26 contains three lines, the translational force, the maximum speed of the sled and the average speed of the sled. From this chart, we see compliance of the test materials where the applied torque is in the 15-26 full scale range, than a period of linear growth between the torque settings of 26 to 35. As the torque is further increased, the material is no longer capable of resisting motion, and free motion of the sled occurs, as represented by the two spiked lines.

What is claimed is:

1. An apparatus for measurement of transient resistance to motion comprising:
    a base;
    first and second pillow blocks attached to said base, said first and second pillow blocks having a horizontal space therebetween;
    a polished linear rod directly connected to said pillow blocks and spanning said horizontal space;
    a movable transport plate assembly securely mounted to, and constrained to move in only one dimension on, said polished linear rod;
    a movable lower substrate having a lower test surface, the lower substrate securely mounted on top of the transport plate assembly;
    a lower substrate holder mounted on said movable transport plate assembly and configured to removably and securely attach said lower substrate to said movable transport plate assembly;
    a stationary upper test assembly having an upper side which is perpendicular to the upper test surface;
    a stationary upper substrate having an upper test surface, the upper substrate securely mounted to the upper test assembly;
    an upper substrate holder mounted to said upper test assembly and configured to removably and securely attach said upper substrate to said upper test assembly;
    a force conducting rod having a first end directly connected to the side of the upper test assembly and extending parallel to the upper test surface;
    a force transducer directly connected to a second end of said force conducting rod, said force transducer being configured to measure a force applied to the force conducting rod by the upper substrate;
    a vertically elongated mount which secures the force transducer, force conducting rod, and upper test assembly to the base;
    a test substance provided between and in direct contact with each of the upper and lower substrates;
    a first normal force applied to the upper test surface, by which a second normal force, equivalent to the first normal force, is created between the upper and lower substrates;
    a torque regulated motor configured to drive the movable transport plate assembly and lower substrate at a speed relative to the stationary upper substrate, a distance between said motor and said base being adjustable;
    a position encoder configured to record a position of the movable transport plate assembly and lower substrate;
    a controller configured to control the torque regulated motor such that the speed and the position are maintained within 0.1% of a target speed and target position, respectively; and
    a data acquisition interface which receives and records each of the force, the torque, the speed, and the position as a function of time;
    wherein said transducer, force conducting rod, and upper test assembly are located on a first plane which is parallel to said base;
    wherein said movable transport assembly and said polished linear rod are located below and parallel to said force conducting rod.

2. The apparatus of claim 1, wherein one or more of the substrates are flexible, conformable, or deformable.

3. The apparatus of claim 1, wherein said movable transport plate assembly is securely mounted to the polished linear rod via bearings.

4. The apparatus of claim 1, wherein the height of said vertically elongated mount and said transducer are adjustable.

5. The apparatus of claim 1, wherein said lower substrate is flexible, is fixedly attached to said movable transport plate assembly at only opposite ends of said lower substrate, is vertically spaced apart from said movable transport plate assembly, and experiences flexing due to said second normal force.

6. The apparatus of claim 1, further comprising two spring-loaded bolts configured to change the height of said motor.

7. The apparatus of claim 1, wherein said upper substrate holder comprises an annular ring configured to fit around said upper test assembly thereby securing a membrane over the upper substrate, said membrane being frictionally engaged by and located between said annular ring and said upper test assembly.

8. The apparatus of claim 1, wherein one or more of the substrates are hydrophobic.

9. The apparatus of claim 1, wherein one or more of the substrates are hydrophilic.

10. The apparatus of claim 1, wherein one or more of the substrates are laminates comprised of films on foams.

11. The apparatus of claim 1, wherein one or more of the substrates are capable of absorbing the test substance.

12. The apparatus of claim 1, wherein one or more of the substrates are chemically or physically reactive with the test substance.

13. A method of measuring the spreading, wetting, slipping, sticking, edge effects, friction, and lubricity of a test substance comprising;
   providing an apparatus comprising a movable transport plate assembly securely mounted to, and constrained to move in only one dimension on, a polished linear rod; a movable lower substrate having a lower test surface, the lower substrate securely mounted on top of the transport plate assembly; a lower substrate holder mounted on said movable transport plate assembly and configured to removably and securely attach said lower substrate to said movable transport plate assembly; a stationary upper test assembly having an upper side which is perpendicular to the upper test surface; a stationary upper substrate having an upper test surface, the upper substrate securely mounted to the upper test assembly; an upper substrate holder mounted to said upper test assembly and configured to removably and securely attach said upper substrate to said upper test assembly; a force conducting rod having a first end directly connected to the side of the upper test assembly and extending parallel to the upper test surface; a force transducer directly connected to a second end of said force conducting rod, said force transducer being configured to measure a force applied to the force conducting rod by the upper substrate; a vertically elongated mount which secures the force transducer, force conducting rod, and upper test assembly to the base; a first normal force applied to the upper test surface, by which a second normal force, equivalent to the first normal force, is created between the upper and lower substrates; a torque regulated motor configured to drive the movable transport plate assembly and lower substrate at a speed relative to the stationary upper substrate, a distance between said motor and said base being adjustable; a position encoder configured to record a position of the movable transport plate assembly and lower substrate; a position encoder configured to record a position of the movable transport plate assembly and lower substrate; a controller configured to control the torque regulated motor such that the speed and the position are maintained within 0.1% of a target speed and target position, respectively; and a data acquisition interface which receives and records each of the force, the torque, the speed, and the position as a function of time;
   providing said test substance provided between and in direct contact with each of the upper and lower substrates;
   varying the speed at a frequency such that the position oscillates about a center position;
   recording the force and torque as a function of time throughout the step of varying; and
   analyzing the recorded force, speed and torque as a function of time to determine the spreading, wetting, slip-stick, edge effects, friction, and lubricity of the test substance.

14. The apparatus of claim 13, wherein one or more of the substrates are flexible, conformable, or deformable.

15. The apparatus of claim 13, wherein one or more of the substrates are capable of absorbing the test substance.

16. The apparatus of claim 14, further comprising analyzing the recorded force and torque as a function of time to determine the spreading, wetting, slip-stick, edge effects, friction, and lubricity of the test substance as a function of the absorption of the test substance by the one or more substrates.

17. The apparatus of claim 13, wherein one or more of the substrates are chemically or physically reactive with the test substance.

18. The apparatus of claim 16, further comprising analyzing the recorded force and torque as a function of time to determine the spreading, wetting, slip-stick, edge effects, friction, and lubricity of the test substance as a function of the reactivity of the test substance by the one or more substrates.

* * * * *